(12) United States Patent
Sakai et al.

(10) Patent No.: US 8,463,383 B2
(45) Date of Patent: Jun. 11, 2013

(54) PORTABLE ASSEMBLIES, SYSTEMS, AND METHODS FOR PROVIDING FUNCTIONAL OR THERAPEUTIC NEUROSTIMULATION

(75) Inventors: Johnathan L. Sakai, Fairview Park, OH (US); Maria E. Bennett, Lyndhurst, OH (US); Joseph W. Boggs, II, Carrboro, NC (US); Robert B. Strother, Willoughby Hills, OH (US); Geoffrey B. Thrope, Shaker Heights, OH (US); Kenneth P. Rundle, Independence, OH (US); Stuart F. Rubin, Orange Village, OH (US)

(73) Assignee: NDI Medical, Inc., Cleveland, OH (US)

( * ) Notice: Subject to any disclaimer, the term of this patent is extended or adjusted under 35 U.S.C. 154(b) by 702 days.

(21) Appl. No.: 12/462,384

(22) Filed: Aug. 3, 2009

(65) Prior Publication Data
US 2010/0036445 A1    Feb. 11, 2010

Related U.S. Application Data

(60) Provisional application No. 61/137,652, filed on Aug. 1, 2008.

(51) Int. Cl.
*A61N 1/18* (2006.01)

(52) U.S. Cl.
USPC ............. 607/34; 607/37; 607/46; 607/118; 607/152

(58) Field of Classification Search
USPC ............. 607/46, 152, 149, 129, 119, 118, 607/117, 116
See application file for complete search history.

(56) References Cited

U.S. PATENT DOCUMENTS

| | | | |
|---|---|---|---|
| 3,939,841 A | 2/1976 | Dohring | |
| 3,943,932 A | 3/1976 | Woo | |
| 4,398,545 A | 8/1983 | Wilson | |
| 4,416,276 A * | 11/1983 | Newton et al. | 606/35 |
| 4,512,351 A | 4/1985 | Pohndorf | |
| 5,397,338 A | 3/1995 | Grey et al. | |
| 5,449,378 A | 9/1995 | Schouenborg | |
| 5,549,655 A | 8/1996 | Erickson | |
| 5,607,461 A | 3/1997 | Lathrop | |

(Continued)

FOREIGN PATENT DOCUMENTS

| | | |
|---|---|---|
| EP | 0743533 | 11/1996 |
| JP | 2001-190696 | 7/2001 |

(Continued)

OTHER PUBLICATIONS

International Preliminary Report on Patentability; PCT/US2009/00440; Feb. 1, 2011.

(Continued)

*Primary Examiner* — Christopher D Koharski
*Assistant Examiner* — Natasha Patel

(57) ABSTRACT

Neurostimulation assemblies, systems, and methods make possible the providing of short-term therapy or diagnostic testing by providing electrical connections between muscles and/or nerves inside the body and stimulus generators and/or recording instruments mounted on the surface of the skin or carried outside the body. Neurostimulation assemblies, systems, and methods may include a carrier and an electronics pod, the electronics pod including stimulation generation circuitry and user interface components. A power source and/or flash memory may be incorporated in neurostimulation assembly and/or the return electrode. The assemblies, systems, and methods are adapted to provide coordinated neurostimulation to multiple regions of the body.

7 Claims, 10 Drawing Sheets

U.S. PATENT DOCUMENTS

| | | | |
|---|---|---|---|
| 5,721,482 | A | 2/1998 | Benvegar et al. |
| 5,857,968 | A | 1/1999 | Benja-Athon |
| 5,861,015 | A | 1/1999 | Benja-Athon |
| 5,861,016 | A | 1/1999 | Swing |
| 5,948,006 | A | 9/1999 | Mann |
| 5,957,951 | A | 9/1999 | Cazaux et al. |
| 6,016,449 | A | 1/2000 | Fischell et al. |
| 6,016,451 | A | 1/2000 | Sanchez-Rodarte |
| 6,020,082 | A | 2/2000 | Orlando |
| 6,026,328 | A | 2/2000 | Peckham et al. |
| 6,072,299 | A | 6/2000 | Kurle et al. |
| 6,108,579 | A | 8/2000 | Snell et al. |
| 6,200,265 | B1 | 3/2001 | Walsh et al. |
| 6,208,902 | B1 | 3/2001 | Boveja |
| 6,257,906 | B1 | 7/2001 | Price et al. |
| 6,275,737 | B1 * | 8/2001 | Mann ............................. 607/61 |
| 6,338,347 | B1 | 1/2002 | Chung |
| 6,366,809 | B1 | 4/2002 | Olson et al. |
| 6,445,955 | B1 | 9/2002 | Michelson et al. |
| 6,544,189 | B2 * | 4/2003 | Watrous ....................... 600/528 |
| 6,607,500 | B2 | 8/2003 | DaSilva et al. |
| 6,622,037 | B2 | 9/2003 | Kasano |
| 6,687,538 | B1 | 2/2004 | Hrdlicka et al. |
| 6,845,271 | B2 | 1/2005 | Fang et al. |
| 6,904,324 | B2 | 6/2005 | Bishay |
| 6,955,864 | B1 | 10/2005 | Vaisnys et al. |
| 7,031,768 | B2 | 4/2006 | Anderson et al. |
| 7,120,499 | B2 | 10/2006 | Thrope et al. |
| 7,376,467 | B2 | 5/2008 | Thrope et al. |
| 7,571,002 | B2 | 8/2009 | Thrope et al. |
| 8,086,318 | B2 | 12/2011 | Strother et al. |
| 2002/0019652 | A1 | 2/2002 | DaSilva et al. |
| 2002/0077572 | A1 | 6/2002 | Fang et al. |
| 2003/0014088 | A1 | 1/2003 | Fang et al. |
| 2003/0028170 | A1 | 2/2003 | Anderson et al. |
| 2003/0032859 | A1 | 2/2003 | Belson |
| 2003/0065368 | A1 | 4/2003 | Van Der Hoveven |
| 2003/0074030 | A1 | 4/2003 | Leyde et al. |
| 2003/0078633 | A1 | 4/2003 | Firlik et al. |
| 2003/0120259 | A1 | 6/2003 | Mickley |
| 2003/0176908 | A1 | 9/2003 | Lin |
| 2003/0195599 | A1 | 10/2003 | Bishay |
| 2005/0165458 | A1 | 7/2005 | Boveja et al. |
| 2005/0182455 | A1 | 8/2005 | Thrope et al. |
| 2005/0182457 | A1 | 8/2005 | Thrope et al. |
| 2005/0277844 | A1 | 12/2005 | Strother et al. |
| 2006/0004421 | A1 | 1/2006 | Bennett et al. |
| 2007/0032837 | A1 | 2/2007 | Thrope et al. |
| 2007/0123952 | A1 * | 5/2007 | Strother et al. ................. 607/48 |
| 2007/0255153 | A1 | 11/2007 | Kumar et al. |
| 2008/0065182 | A1 | 3/2008 | Strother et al. |
| 2008/0071322 | A1 | 3/2008 | Mrva et al. |
| 2008/0097564 | A1 | 4/2008 | Lathrop |
| 2008/0154335 | A1 | 6/2008 | Thrope et al. |
| 2008/0161874 | A1 | 7/2008 | Bennett et al. |

FOREIGN PATENT DOCUMENTS

| | | |
|---|---|---|
| WO | WO00/07665 | 2/2000 |
| WO | WO2005/079295 | 9/2005 |
| WO | WO2007/136726 | 11/2007 |
| WO | WO2010/014259 | 2/2010 |

OTHER PUBLICATIONS

International Preliminary Report on Patentability; PCT/US09/04440, Apr. 26, 2012.
Office Action for U.S. Appl. No. 10/777,771, dated Nov. 15, 2005.
Office Action for U.S. Appl. No. 11/056,591, dated Sep. 28, 2006.
Office Action for U.S. Appl. No. 11/978,824, dated Dec. 30, 2010.
Office Action for U.S. Appl. No. 11/595,556, dated Mar. 4, 2011.
Office Action for U.S. Appl. No. 11/545,339, dated Sep. 26, 2008.
International Preliminary Report on Patentability, PCT/US07/11867, Oct. 9, 2008.
Office Action for U.S. Appl. No. 11/595,556, dated Aug. 6, 2010.
Neuro Control Corporation, NeuroControl Stlm System Brochure, 2000.
International Preliminary Report on Patentability for PCT/US05/04393, May 16, 2006.
NeuroControl Corporation, The NeuroControl StLM System, "World's First Miniaturized Multi-Channel Programmable Neuromuscular Stimulator" brochure 2000.

* cited by examiner

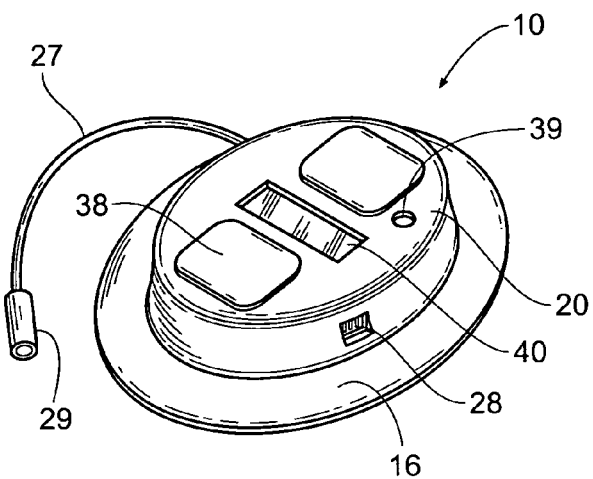
Fig. 1
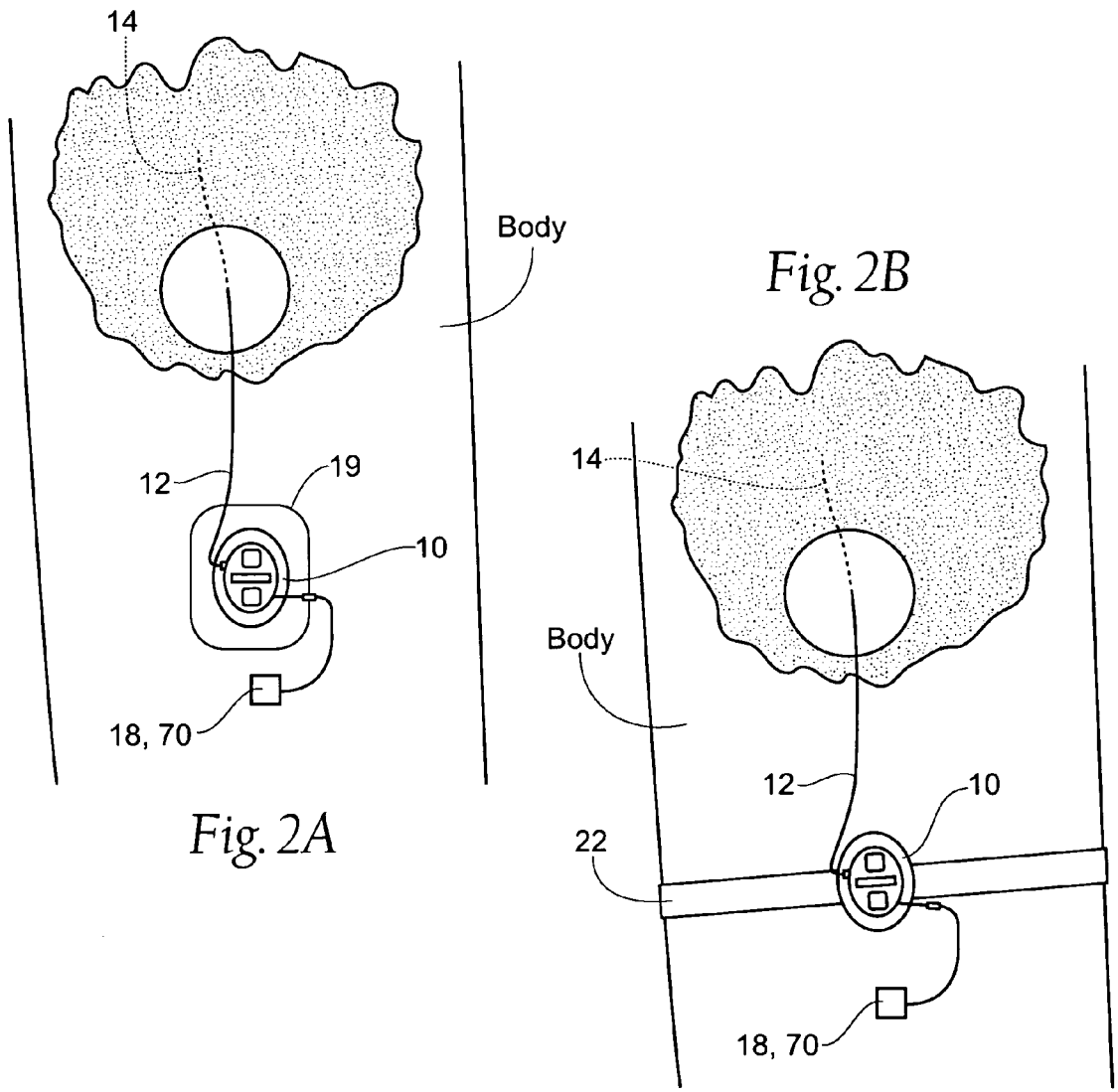
Fig. 2B
Fig. 2A

US 8,463,383 B2

PORTABLE ASSEMBLIES, SYSTEMS, AND METHODS FOR PROVIDING FUNCTIONAL OR THERAPEUTIC NEUROSTIMULATION

RELATED APPLICATIONS

This application claims the benefit of U.S. Provisional Patent Application Ser. No. 61/137,652, filed Aug. 1, 2008, and entitled "Portable Assemblies, Systems, and Methods for Providing Functional or Therapeutic Neurostimulation," which is incorporated herein by reference.

This application is a continuation-in-part of U.S. patent application Ser. No. 11/978,824, filed Oct. 30, 2007, and entitled "Portable Assemblies, Systems and Methods for Providing Functional or Therapeutic Neuromuscular Stimulation," which is a divisional application of U.S. patent application Ser. No. 11/595,556, filed Nov. 10, 2006, and entitled "Portable Assemblies, Systems and Methods for Providing Functional or Therapeutic Neuromuscular Stimulation," which claims the benefit of U.S. Provisional Patent Application Ser. No. 60/801,315, filed May 18, 2006, and entitled "Portable Assemblies, Systems, and Methods for Providing Functional or Therapeutic Neuromuscular Stimulation," which are incorporated herein by reference.

This application is also a continuation-in-part of U.S. patent application Ser. No. 11/056,591, filed Feb. 11, 2005, and entitled "Portable Assemblies, Systems and Methods for Providing Functional or Therapeutic Neuromuscular Stimulation," which claim the benefit of U.S. Provisional Patent Application Ser. No. 60/551,945, filed Mar. 10, 2004, and entitled "Steerable Introducer for a Percutaneous Electrode Usable in Association with Portable Percutaneous Assemblies, Systems and Methods for Providing Highly Selective Functional or Therapeutic Neurostimulation," which are incorporated herein by reference.

This application is also a continuation-in-part of U.S. patent application Ser. No. 11/545,339, filed Oct. 10, 2006, and entitled "Portable Percutaneous Assemblies, Systems and Methods for Providing Highly Selective Functional or Therapeutic Neurostimulation," which is a continuation of U.S. patent application Ser. No. 10/777,771, now U.S. Pat. No. 7,120,499, filed Feb. 12, 2004, and entitled "Portable Percutaneous Assemblies, Systems and Methods for Providing Highly Selective Functional or Therapeutic Neurostimulation," which are incorporated herein by reference.

STATEMENT REGARDING FEDERALLY SPONSORED RESEARCH

This invention was made with government support under grant no. 1R43AR052211-01 awarded by the National Institutes of Health, through the National Institute of Arthritis and Musculoskeletal and Skin Diseases. The Government has certain rights in the invention.

FIELD OF INVENTION

This invention relates to assemblies, systems, and methods for providing neurostimulation to tissue.

BACKGROUND OF THE INVENTION

Neurostimulation, i.e., neuromuscular stimulation (the electrical excitation of nerves and/or muscle to directly elicit the contraction of muscles) and neuromodulation stimulation (the electrical excitation of nerves, often afferent nerves, to indirectly affect the stability or performance of a physiological system) and brain stimulation (the stimulation of cerebral or other central nervous system tissue) can provide functional and/or therapeutic outcomes. While existing systems and methods can provide remarkable benefits to individuals requiring neurostimulation, many quality of life issues still remain. For example, existing systems perform a single, dedicated stimulation function, and are unable to operate in a fashion to provide coordinated stimulation to multiple regions of a body. Furthermore, these controllers are, by today's standards, relatively large and awkward to manipulate and transport.

There exist both external and implantable devices for providing neurostimulation in diverse therapeutic and functional restoration indications. These neurostimulators are able to provide treatment therapy to individual portions of the body. The operation of these devices typically includes the use of an electrode placed either on the external surface of the skin and/or a surgically implanted electrode. In the case of external neurostimulators, surface electrodes and/or percutaneous lead(s) having one or more electrodes are used to deliver electrical stimulation to the select portion(s) of the patient's body.

Several clinical and technical issues associated with surface electrical stimulation have prevented it from becoming a widely accepted treatment method. First, stimulation of cutaneous pain receptors cannot be avoided resulting in stimulation-induced pain that limits patient tolerance and compliance. Second, electrical stimulation is delivered at a relatively high frequency to prevent stimulation-induced pain, which leads to early onset of muscle fatigue. Third, it is difficult to stimulate deep muscles with surface electrodes without stimulating overlying, more superficial muscles resulting in unwanted stimulation. Finally, clinical skill and intensive patient training is required to place surface electrodes reliably on a daily basis and adjust stimulation parameters to provide optimal treatment. The required daily maintenance and adjustment of a surface electrical stimulation system is a major burden on both patient and caregiver.

It is time that systems and methods for providing neurostimulation address not only specific prosthetic, functional, or therapeutic objections, but also address the quality of life of the individual requiring neurostimulation, including the ability to operate a neurostimulation device without concern for replenishing a power source, and to provide coordinated stimulation to multiple regions of a body.

SUMMARY OF THE INVENTION

The invention provides improved assemblies, systems, and methods for providing prosthetic or therapeutic neurostimulation.

One aspect of the invention provides portable, percutaneous or surface mounted neurostimulation assemblies, systems and methods that provide electrical connections between muscles or nerves inside the body and stimulus generators and/or recording instruments temporarily mounted/positioned on the surface of the skin or carried outside the body.

The assemblies, systems, and methods may, in use, be coupled by percutaneous leads to electrodes, which are implanted below the skin surface, or, alternatively, may be coupled to surface mounted electrode(s), or both, and positioned at a targeted tissue region or regions. The neurostimulation assemblies, systems, and methods apply highly selective patterns of neurostimulation only to the targeted region or regions, to achieve one or more highly selective therapeutic and/or functional and/or diagnostic outcomes. The patterns can vary according to desired therapeutic and/or diagnostic objectives. The indications can include, e.g., the highly selective treatment of pain or muscle dysfunction, and/or the highly selective promotion of healing of tissue or bone, and/or the highly selective diagnosis of the effectiveness of a prospective functional electrical stimulation treatment by a future, permanently implanted device. In addition, the controller interface from the user to the neurostimulation assemblies, systems, and methods may be wireless or may be manually entered via a user interface on the assembly.

The neurostimulation assemblies, systems, and methods may comprise a disposable patch or carrier. The carrier can be readily carried, e.g., by use of a pressure-sensitive adhesive and/or covered by a covering bandage, such as Tegaderm™, without discomfort and without affecting body image on, for example, an arm, a leg, or torso of an individual. In place of worn on the skin, the patch or carrier may also be carried by the patient, such as in a pocket, or secured to clothing, a bed, or to movable devices to allow for patient mobility, or alternatively, the carrier may include a strap to hold the assembly on an arm, a leg, or a torso, for example.

The carrier carries an electronics pod, which generates the desired electrical current patterns. The pod houses microprocessor-based, programmable circuitry that generates stimulus currents, time or sequence stimulation pulses, monitors system status, and logs and monitors usage, for example. The electronics pod may be configured, if desired, to accept wireless RF based commands for both wireless programming and wireless patient control.

The electronics pod may also include one or more connection regions, to physically and electrically couple percutaneous electrode leads and a surface mounted return electrode to the circuitry of the electronics pod, provide access for a programming/communication device, and alternatively provide for networking of multiple assemblies.

The electronics pod and/or the return electrode may further include a power source. The power source provides power to the electronics pod for the predetermined functional life of the neurostimulation assemblies, systems and methods, which may be hours, days, weeks, months, or up to years. The power source may comprise a removable or non-removable, replaceable or non-replaceable, and rechargeable or non-rechargeable power source.

A communication/programming device may be plugged into a mating communications interface on the electronics pod, or the neurostimulation assemblies, systems and methods may include a wireless interface to an external device. Through this link, a caregiver or clinician can individually program the operation of a given electronics pod. If need be, the caregiver or clinician can modulate various stimulus parameters in real time.

Another aspect of the invention provides assemblies, systems, and methods for providing neurostimulation comprising at least one electrode, a disposable carrier sized and configured to be worn by a user, an electronics pod carried on-board the carrier, the electronics pod including circuitry configured to generate a stimulation pulse to the electrode, and a power source electrically coupled to the circuitry, the power source providing power to the circuitry for the predetermined functional life of the assemblies, systems, and methods.

The electronics pod may also include a visual output, such as a display carried on-board the electronics pod and/or visible through the electronics pod. The visual output can also be provided by an illumination source that illuminates at least a portion of the electronics pod.

Another aspect of the invention proves systems and methods comprising a neurostimulation assembly. The assembly may include at least one electrode sized and configured for implantation in a targeted neural or muscular tissue region, a lead electrically coupled to the electrode and including a connection element adapted to electrically couple to a carrier, the carrier sized and configured to be carried by the patient, an electronics pod removably carried on-board the carrier, the electronics pod including circuitry configured to generate a stimulation pulse, a power source electrically coupled to the circuitry, a return electrode adapted to be electrically coupled to the carrier, instructions prescribing the release and replacement of the return electrode according to a preset schedule, and an electrode connection element carried on-board the carrier that is electrically coupled to the electronics pod, the electrode connection element being sized and configured to electrically engage at least a portion of the connection element of the lead to electrically couple the electrode to the electronics pod to percutaneously apply the stimulation pulse to the tissue region.

In one embodiment, the carrier is sized and configured to hold the power source. In another embodiment, the return electrode is sized and configured to hold the power source. The power source may be at least on of a non-removable and non-replaceable and non-rechargeable power source.

Another aspect of the invention provides assemblies, systems, and methods comprising a surface mounted electrode. The electrode comprises a top layer and a bottom layer, the bottom layer adapted to provide electrical contact and adhesion to a patient, a power source positioned between the top layer and the bottom layer, and electrically coupled to the bottom layer and a cable assembly, and a connector electrically coupled to the cable assembly, the cable assembly and connector adapted to provide electrical contact between the power source and a neurostimulation assembly.

In one embodiment, at least one conductor of the cable assembly comprises a carbon-fiber wire. The carbon-fiber wire may be adapted to make intimate contact with the bottom layer.

In one embodiment, the power source is adapted to be sandwiched between layers of non-conductive material. The layers of non-conductive material and the power source sandwiched there between may also be sandwiched between the top layer and the bottom layer. The power source comprises a flexible power source, and may comprises a capacity of about 1 mA-hr to about 1000 mA-hr.

In one embodiment, the surface mounted electrode further includes non-volatile memory positioned between the top layer and the bottom layer.

Another aspect of the invention provides assemblies, systems, and methods comprising providing a surface mounted electrode as defined in claim 1, placing the electrode on a tissue surface, and coupling the electrode to a neurostimulation assembly.

Other features and advantages of the inventions are set forth in the following specification and attached drawings.

BRIEF DESCRIPTION OF THE DRAWINGS

FIG. 1 is a perspective view of a neurostimulation assembly that provides electrical connections between muscles and/or nerves inside the body and stimulus generators temporarily mounted on the surface of the skin or carried outside the body.

FIGS. 2A and 2B are views of the neurostimulation assembly shown in FIG. 1 worn or carried on a temporary basis on an external skin surface of the body.

Although the disclosure hereof is detailed and exact to enable those skilled in the art to practice the invention, the physical embodiments herein disclosed merely exemplify the invention which may be embodied in other specific structures. While the desired embodiment has been described, the details may be changed without departing from the invention, which is defined by the claims.

DESCRIPTION OF THE PREFERRED EMBODIMENTS

The various aspects of the invention will be described in connection with providing neurostimulation for prosthetic or therapeutic purposes. That is because the features and advantages that arise due to the invention are well suited to this purpose. Still, it should be appreciated that the various aspects of the invention can be applied to achieve other objectives as well.

I. Neurostimulation Assembly Overview

FIG. 1 shows an exemplary embodiment of neurostimulation assembly 10. As FIGS. 2A and 2B show, the neurostimulation assembly 10 may be sized and configured so that, in use, it can be conveniently worn on a temporary basis. By "worn," it is meant that the assembly 10 may be removably skin mounted (see FIG. 2A), or may also be carried by the patient (i.e., user), or secured or strapped (see FIG. 2B) to the patient's arm, leg, waist, clothing, a bed, or to movable devices to allow for patient mobility. By "temporary," it is meant that the presence of the neurostimulation assembly 10 can be well tolerated without discomfort for a period of time from several hours to a month or two, or more, after which the neurostimulation assembly 10 can be removed and discarded. During the period of use, the neurostimulation assembly 10 may be removed and reattached for hygiene maintenance. The assembly 10 may be constructed in a manner to conform to the IPX8 standard for water ingress. The assembly 10 may be constructed in a manner to conform to lower water ingress standards as well, for limited water contact applications.

Figure 3:
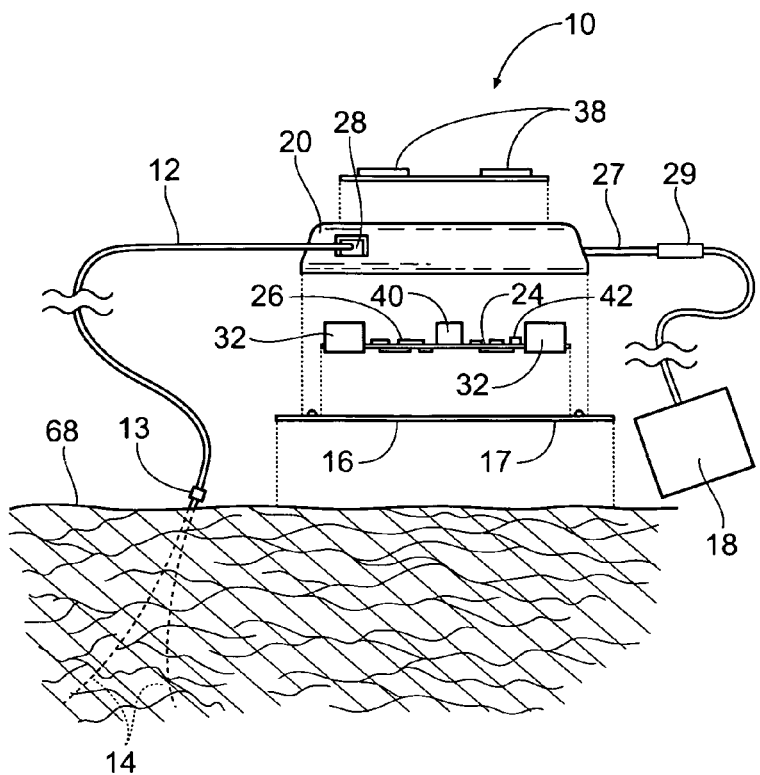
FIG. 3 is an exploded side view of an embodiment of the neurostimulation assembly shown in FIG. 1, showing its coupling to percutaneous leads to electrodes, which are implanted below the skin surface in a targeted tissue region or regions.

As FIG. 3 shows, the neurostimulation assembly 10 is, in use, releasably coupled to a lead 12, including an extension lead 12, with the lead 12 coupled to electrode(s) 14 at connector 13. The electrodes 14 may be implanted, e.g., percutaneously, below the skin surface in a targeted tissue region or regions. The tissue region or regions are targeted prior to implantation of the electrodes 14 due to their muscular and/or neural morphologies in light of desired therapeutic and/or functional and/or diagnostic objectives.

In use, the neurostimulation assembly 10 generates and distributes electrical current patterns through the lead 12 to the electrodes 14 and back to a return electrode. In this way, the neurostimulation assembly 10 applies highly selective patterns of neurostimulation only to the targeted region or regions, to achieve one or more highly selective therapeutic and/or diagnostic outcomes. As will be described in greater detail later, the inputs/stimulation parameters can vary according to desired therapeutic and/or diagnostic objectives. As non-limiting examples, the outcomes can comprise the highly selective treatment of pain or muscle dysfunction, and/or the highly selective promotion of healing of tissue or bone, and/or the highly selective diagnosis of the effectiveness of a prospective functional electrical stimulation treatment.

The neurostimulation assembly 10 will enable a physician to deliver a lead 12 and electrode 14, such as a fine wire percutaneous lead 12 and electrode(s) 14 to target locations via a hypodermic needle and send the patient home with a skin-mounted or carried or strapped miniature neurostimulation assembly 10. By delivering the therapy via percutaneous electrodes 14, the barriers associated with surface stimulation, including cutaneous pain and unreliable electrode placement are eliminated. The use of percutaneous electrodes allows the selective, comfortable, and consistent activation of the muscle(s) (and/or their innervating nerves) into which the electrode(s) 14 are implanted. Furthermore, by securing the neurostimulation assembly 10 to the skin near the treatment site, or strapped near the treatment site, for example, and eliminating lengthy external cables, the assembly 10 may enhance the ease of use of electrical stimulation therapy, improving clinical acceptance and patient compliance.

II. Desirable Technical Features

The neurostimulation assembly 10 can incorporate various technical features to enhance its usability, which will now be described.

A. The Carrier

In its most basic form (see FIGS. 1 and 3), the neurostimulation assembly 10 comprises a disposable patch or carrier 16. The carrier 16 desirably is sized and configured as a compact, lightweight, and flexible assembly made, e.g., of an inert, formed or machined plastic or metal material.

In a representative embodiment, the carrier 16 may be generally oval and measure about 50 mm to about 80 mm in height, and about 30 mm to about 60 mm in width, and about 10 mm to about 20 mm in depth, and more particularly about 60 mm to about 70 mm in height, and about 40 mm to about 50 mm in width, and about 12 mm to about 18 mm in depth, or more or less. The neurostimulation assembly 10 may weigh about 30 grams to about 50 grams, and more particularly about 40 grams, or more or less.

It is to be appreciated that the neurostimulation assembly 10 and associated carrier 16 may comprise a variety of sizes, shapes, and weights, for different applications and/or to increase or decrease the mounting surface area. At this size, the carrier 16 can be readily worn or carried without discomfort and in a cosmetically acceptable way (as FIGS. 2A and 2B show). The flexible carrier material and shape will allow the neurostimulation assembly 10 to be positioned on curved surfaces of the body, such as an arm, shoulder, leg, stomach, and/or back, for example.

B. Securing the Neurostimulation Assembly

The undersurface of the carrier 16 may include an adhesive region 17. The function of the optional adhesive region 17 is to temporarily secure the neurostimulation assembly 10 to an external skin surface during use. For example, an inert, conventional pressure sensitive adhesive or tape can be used. Desirably, the dermal adhesive region contains a bacteriostatic sealant that prevents skin irritation or superficial infection, which could lead to premature removal.

In place of, or in conjunction with the adhesive region 17, covering bandage(s) 19 may be used to temporarily secure the neurostimulation assembly 10 in place on the external skin surface. Covering bandages 19 may also be used to temporarily secure an extension lead 12, and the electrode(s) 14 and the extension lead connector 13, to the skin surface. The use of one or more skin-like covering bandages 19 eliminates concerns over lead maintenance and keeps the assembly 10, extension lead 12, and electrodes 14 from snagging during bathing, dressing, or personal grooming, for example.

In place of, or in conjunction with, the adhesive region 17, and/or covering bandage(s) 19, the assembly 10 may be held in place with the use of a strap 22. The strap may incorporate velco and/or elastic, for example, to allow flexibility and comfort when temporarily securing the neurostimulation assembly 10 to the desired body region.

C. The Electronics Pod

The carrier 16 may further carry an electronics pod 20, which generates the desired electrical current patterns and may incorporate a connector 29 for communication/programming with an external programming system or controller 46.

As FIG. 3 shows, the electronics pod 20 can comprise a component or an assembly, such as a molded plastic component or assembly that can be sealably secured to the carrier 16. In an alternative embodiment, the electronics pod 20 may be removable and replaceable on the carrier 16. Having an electronics pod 20 that can be separated from the carrier 16 may be desired when the need to replace a carrier 16, or the electronics pod 20, during a course of treatment is necessary. For example, replacement of a carrier 16 without replacement of the electronics pod 20 may be desired if the anticipated length of use of the neurostimulation assembly 10 is going to be long enough to expect a degradation of adhesive properties of the adhesive region 17, (if used), or if the adhesive region 17 includes a return electrode, and may undergo, with use, degradation of adhesive properties and/or electrical conductivity.

Regardless of whether the electronics pod 20 is removable from the carrier 16, the pod 20 houses microprocessor-based (microcontroller) circuitry 24 that generates stimulus waveforms, time or sequence stimulation pulses, logs and monitors usage, monitors system status, and can communicate directly to the clinician or indirectly through the use of an external programmer or controller. As a representative example, the stimulation desirably has a biphasic waveform (net DC current less than 10 microAmps), adjustable from about 0 mA to about 20 mA based on electrode type and the tissue type being stimulated, pulse durations adjustable from about 5 microseconds or less up to about 500 microseconds or more, and a frequency programmable from about 1 Hz to about 150 Hz. Most muscle stimulation applications will be in the 10 Hz to about 20 Hz region, and pain management may use the higher frequencies. The stimulus current (amplitude) may be user selectable and the pulse duration may be limited to clinician selectable.

The circuitry 24 desirably includes non-volatile memory, such as a flash memory device or an EEPROM memory chip to carry embedded, programmable code 26. The code 26 expresses the pre-programmed rules or algorithms under which the stimulation timing and command signals are generated. The circuitry 24 can be carried in a single location or at various locations in and/or on the pod 20, and/or return electrode 70, and may be fabricated on flexible or flex-rigid PC board using a very high density technique.

D. Lead Connectors

As FIGS. 1 and 3 show, the electronics pod 20 also includes one or more connectors 27, 28, 30. The function of the lead connector 27 is to physically and electrically couple the terminus of the return electrode 18 to the circuitry 24 of the electronics pod 20. In the illustrated embodiments, the lead connector 27 comprises a pig-tail cable extending off the electronics pod 20 and ending with a connector 29. It is to be appreciated that the pig-tail cable could-extend off the carrier 16 as well. It is also to be appreciated that the connector 29 could be integral with the electronics pod 20 or carrier 16 as well, i.e., without the pig-tail cable.

Connector 28 physically and electrically couples the terminus of the lead 12, or extension if used, to the circuitry 24 of the electronics pod 20. When multiple channels are used, the connector 28 is able to distribute the electrical current patterns in channels, i.e., each electrode 14 comprises a channel, so that highly selective stimulation patterns can be applied through multiple electrodes 14. One or more channels may be provided, i.e., two electrodes 14.

Figure 5:
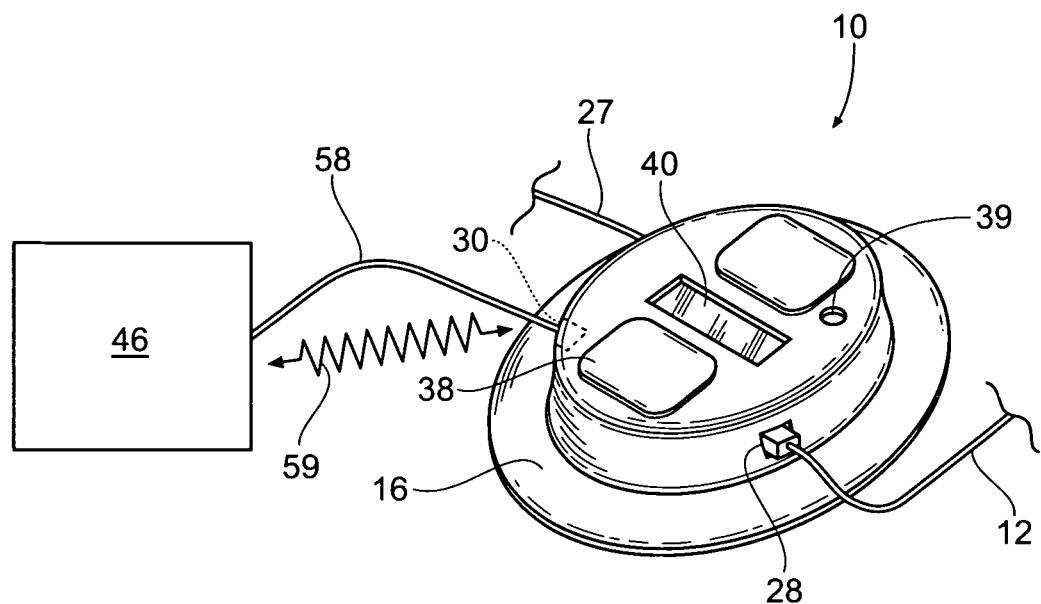
FIG. 5 is a perspective view of an embodiment of a neurostimulation assembly of the type shown in FIG. 1 coupled to an external programming/communication instrument.
Figure 6:
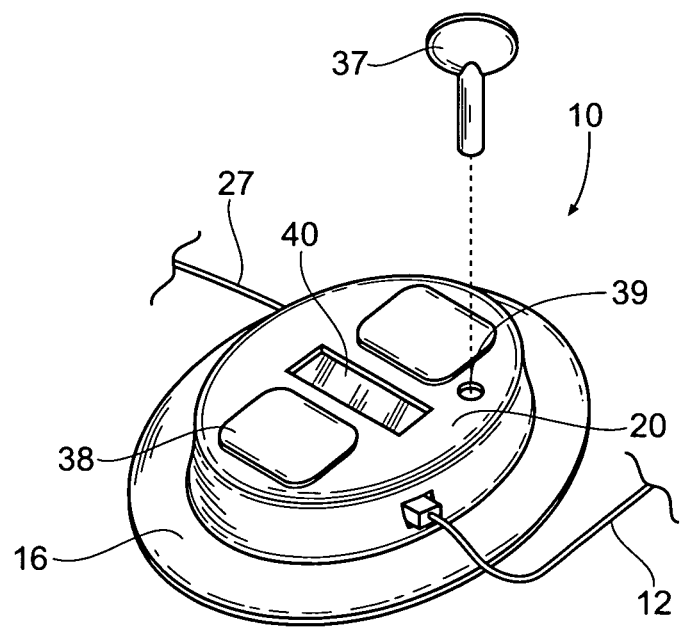
FIG. 6 is a perspective view of an embodiment of a neurostimulation assembly of the type shown in FIG. 1 in association with a programming mode key adapted to allow a clinician access to a programming mode to adjust stimulus parameters and gather/view usage data.

Connector 30 may be provided as an option for physically and electrically coupling a communication/programming device 46 to the circuitry 24 of the electronics pod 20, i.e., connector 30 can serve as a communication interface. As FIG. 5 shows, the connector 30 can be used to couple to an external programming device or computer 46. Through this link 58, information and programming input can be exchanged and data can be downloaded from the electronics pod 20. This connector may be normally plugged with a rubber seal and only accessed during device communication/programming.

It should be appreciated, of course, that instead of using a cable interface 58, as shown, a wireless link 59 (e.g., RF magnetically coupled, infrared, or RF for example) could be used to place the electronics pod 20 in communication with an external programming device 46 or computer.

The connectors 28, 29, and 30 may be touch proof and/or water proof connectors to help maintain a consistent and reliable electrical connection. Each connector may be labeled with a number or other indicia to identify the channel of the electronics circuitry 24 that is coupled to each connector.

It is to be appreciated that alternative embodiments are possible. Coupling the extension lead 12, return electrode 18, 70, and device 46 to the electronics pod 20 or carrier 16, can be accomplished by a locking motion, a button, or a lever arm, or an Allen drive that is pushed, or slid, or pulled, or twisted, for example.

E. The Power Source

1. Internal Power Source

One embodiment of the power source 32 can be described as a self-contained, limited life power source.

The power source 32 may comprise one or more known power sources, such as capacitor(s) or battery(ies) 32, e.g., an alkaline, lithium, or Silver Oxide battery to provide the power to the electronics pod 20 (see FIG. 3). The power source may be selected based on the predetermined functional life of the assembly 10. As non-limiting examples, embodiments of the assembly 10 may be preconfigured for a functional life of one hour, day, week, month, year, two years, five years, or more or less. The power source 32 capacity may be sized to match the stimulation output capabilities of the assembly 10 for a predetermined amount of time, such as an hour, day, week, month, or year(s), for example. As another non-limiting example, one embodiment of the assembly 10 may be preconfigured for a functional life of two months. The power source 32 capacity would be sized to match the stimulation output capabilities of the assembly 10 for at least the two month period. It is to be appreciated that the neurostimulation assembly 10 may incorporate a wide range of power source capacities to reduce or extend the predetermined functional life of the assembly.

The circuitry 24 may be used to electronically store information about the power source 32. The circuitry 24 may include a non-volatile memory 26 to store the power source and other information. The estimated remaining capacity of the power source 32 may be stored. The circuitry 24 may also identify the total power usage (service time) provided to date by the power source.

In one embodiment, the power source 32 may be non-replaceable, non-removable, and/or non-rechargeable. The neurostimulation assembly 10 may not require or allow the user to replace the power source 32 for the entire length of the temporary therapy, e.g., the power source capacity may be sized to function for the predetermined functional life of the assembly and/or the treatment period. Other external stimulators require that the user replace and/or recharge a battery as frequently as once per week. This task can be difficult for post-stroke patients who have compromised hand function on the hemiplegic side.

The power source 32 may be inaccessible to battery replacement. In one embodiment, the power source 32 may be secured within the electronics pod 20. The electronics pod 20 may comprise a molded plastic housing, the housing may include multiple pieces and may be made inaccessible by sonic welding, gluing, or other permanent fastening methods, to secure the housing together.

A power budget for the circuitry 24 was developed based on the neurostimulation assembly's performance specifications and expected operating characteristics of the key circuit components (based on component specifications). Based on the power budget, a 500 mA-hr to 600 mA-hr primary cell battery may provide a service life sufficient for the neurostimulation assembly's performance specifications and expected operating characteristics, although it is to be appreciated that smaller and/or larger capacities may be used, such as from about 10 mA-hr to about 1000 mA-hr, or more or less. Combined with the desired size and shape of the neurostimulation assembly 10, Lithium primary cell types available from domestic suppliers were considered candidates. In one embodiment, representative battery configurations include two L92 (AAA) 1.5V Li/FeS$_2$ cells in series (each cell is 10 mm diameter×44 mm long); or four ⅓N (⅓ 'N' cell size) 3.0V Li/MnO$_2$ cells in parallel (each cell is 11.5 mm diameter×10.6 mm long).

2. External Power Source

In one embodiment, the return electrode 70, e.g., surface electrode, may include an embedded power source 72, and optionally non-volatile memory, such as flash memory 73. The return electrode 70 may be adapted to provide power and a return path, and optionally stimulus parameters stored in the memory 73, for the neurostimulation assembly 10. The return electrode 70 may be adapted to provide an electrical connection to the patient, and provide power to the neurostimulation assembly 10.

Figure 16:
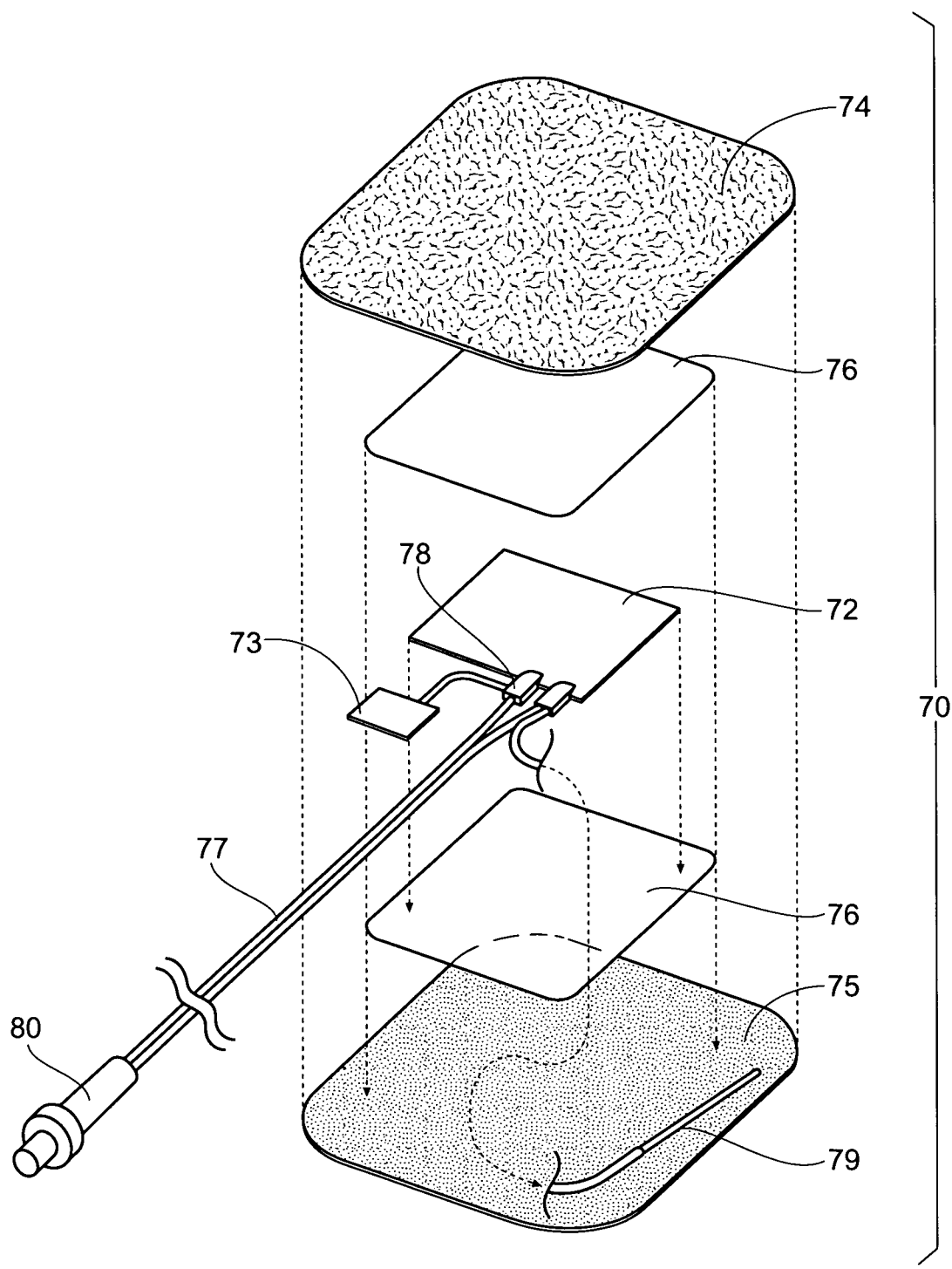
FIG. 16 is an exploded view of one embodiment of a surface return electrode incorporating a powers source and an optional memory chip.

One embodiment of the return electrode 70 shown in FIG. 16 may comprise a top layer 74 and a bottom layer 75. The top and bottom layers may be typical of the construction of TENS/NMES return surface electrodes. The top layer 74 may be an adhesive-backed fabric, for example, such as a non-woven (i.e., non-porous) medical tape. The bottom layer 75 may be a conductive hydrogel, which provides electrical contact and adhesion to the patient. The hydrogel may be selected to provide optimal adhesion and electrical properties for desired applications.

The power source 72 may comprise a thin flexible power source, such as is available from Solicore (Lakeland, Fla.). As a non-limiting example, a 25×29×0.5 mm flexible power source with a capacity of 10 mA-hr may be used, although other dimensions and capacities are within the scope of the invention for a variety of applications (e.g., 1 mA-hr to 1000 mA-hr). The power source 72 and/or the optional flash memory 73 may be positioned between the top and bottom layers 74, 75. The power source 72 and the optional-flash memory 73 may also be sandwiched between one layer folded or two separate layers, for example, of non-conductive material 76, such as an envelope of flexible film. This sandwich of two non-conductive layers and the power source, and optional flash memory, may then be positioned between the top and bottom layers 74, 75.

A cable assembly 77 may be electrically coupled, e.g., soldered, to exposed terminals 78 of the power source 72, which may also be laminated between the non-conductive material 76. Processes such as pressure-sensitive adhesive, overmolding or hot lamination may be used to achieve this state. One conductor 79 of the cable assembly 77 may comprise a carbon-fiber wire, for example, and may exit the laminated assembly and make intimate contact with the bottom hydrogel layer 75. The cable assembly 77 may also provide the electrical connection in common with the power source's negative contact. A connector 80, such as a touch proof and/or water proof connector 80, provides electrical contact between the neurostimulation assembly 10 and the return electrode 70.

As previously described, optionally, a flash memory chip 73 may be included in the return electrode 70. The memory 73 may, for example, provide a predetermined set of stimulus parameters for the neurostimulation assembly 10. This would allow the disposable power source/return electrode 70 to also provide the prescription of the stimulus to be delivered.

The novel combination of a power source and return electrode allows the neurostimulation assembly 10 to be reduced in size as no internal power source is required for the assembly 10. The synergism of integrating the power source 72 with the return electrode 70 is clear as both may be limited life, disposable items.

The optional inclusion of embedded memory 73, such as a flash memory chip, may permit the clinician to prescribe a predetermined set of stimulus parameters with just the selection of the proper return electrode.

The return electrode with embedded power source takes advantage of one example of the usage of the neurostimulation assembly 10, wherein the patient may be changing their return electrode at predetermined periods, such as every day, or days, or week, or weeks, or months, to provide a renewed source of power with each application. This method allows the neurostimulation assembly 10 to be used indefinitely, as long as a sufficient supply of return electrodes 70 is prescribed to the patient.

F. The User Interface

The assembly 10 as shown in FIGS. 1 and 3 desirably includes one or more features that provide an interface mechanism for the patient and/or the clinician. The interface feature allows for the input and output of neurostimulation assembly information, such as stimulus regime parameters and system status, and the interface may be manual, audio, or visual, or a combination. For example, the electronics pod 20 may include control means 38, e.g., two button controls, to allow the patient to control stimulation amplitude setting or some other stimulus intensity adjustment (up-down; plus-minus; etc.). The electronics pod 20 may also be adapted to interface with a programming mode key 37, e.g., a magnet, or a paper clip access switch, for example, to provide control for the clinician to access clinician controllable settings through the control means 38, such as the stimulus pulse duration and/or stimulus frequency and/or stimulus amplitude, for example. As can be seen, the assembly 10 may include a slot or recess 39 adapted to accept the programming mode key 37. The programming mode key 37 desirably is in place in order to switch the neurostimulation assembly 10 into the programming mode and access clinician controllable settings.

Table 1 below provides possible stimulus parameter settings. It is to be appreciated that more or less Stimulus Parameters, different ranges of Assembly Capabilities, and optional Methods of Programming are all within the scope of the invention. Table 1 is only intended as an example of possible settings and capabilities of the neurostimulation assembly 10.

TABLE 1

| Stimulus Parameters | Neurostimulation Assembly Capabilities | Methods of Programming |
| --- | --- | --- |
| Amplitude, sustained | 2-20 mA | Clinician programmable |
| Pulse Duration, sustained | 10-200 μsec | Clinician programmable |
| Frequency | 5-80 Hz | Factory programmable |
| Duty Cycle | 10-100% | Factory programmable |
| Ramp Times | 0-60 seconds | Factory programmable |
| Duty Cycle Period | 15-900 seconds | Factory programmable |
| Session Duration | 1 minute - continuously | Factory programmable |
| # of Sessions per Day | 1-1023 sessions | Factory programmable |
| Pause Between Sessions | 1-1023 minutes | Factory programmable |

In use, the clinician may be able to program the stimulus intensity by inserting the programming key 37 (e.g., a small magnet) into the slot 39 molded into the electronics pod 20. Once the key 37 is inserted, the clinician may use pushbuttons 38 on the assembly 10 to evaluate the patient's response to stimulus intensity settings preconfigured in the assembly. A display 40, e.g., an LCD or LED display on the top of the assembly shows the stimulus intensity being delivered. The clinician then selects the optimal stimulus intensity for the patient from the available settings.

When the programming key 37 is not inserted, the neurostimulation assembly 10 is in the patient mode and stimulus is automatically provided at the stimulus intensity programmed by the clinician. The patient can use the two pushbuttons 38 on top of the assembly to turn the stimulation off or make minor changes to the stimulus intensity programmed by the clinician.

The particular setting level can be displayed using the display 40 to visually identify to the patient the setting level, and to allow the patient to record the setting within a therapy diary, which could then be presented to a physician for review. The operating modes and stimulus parameters may be entered manually using the control means 38 and/or 37, and easily interpreted via the visual output or feedback display 40. In one embodiment, the setting level is a combination of pulse duration and amplitude, the specifics of which are unknown to the patient. The display 40 may also provide a data read-out function for the clinician. For example, the display 40 may provide information such as the total duration of stimulus provided, the average or median stimulus level selected by the patient, and perhaps the total duration of no stimulation provided.

The display 40 may also provide status information, such as power source status or system status. For power source status, the stimulation assembly 10 may indicate the power source 32 has limited power remaining, or that the power source has provided its maximum amount of power, as non-limiting examples. For system status, the stimulation assembly 10 may indicate the electrical connections to the extension lead 12, electrodes 14, or return electrode 18 are not working, as non-limiting examples.

In addition to or in place of the visual feedback display 40, visual output or feedback may also be provided by an illuminating electronics pod 20, or portions of the electronics pod. The pod 20 may comprise a material, e.g., a semi-transparent material, able to allow an illumination source 42, such as one or more LEDs, to create a "glowing" or "illuminated" appearance. The illumination source 42 may be coupled to the circuitry 24 within the electronics pod 20. Status information can be visually provided to the user by using various blinking or pulsing configurations, illumination brightness, changing colors, or any combination, for example. As with the display 40, status information may include power source status and system status.

III. Representative Neurostimulation Assembly Circuitry

Figure 7:
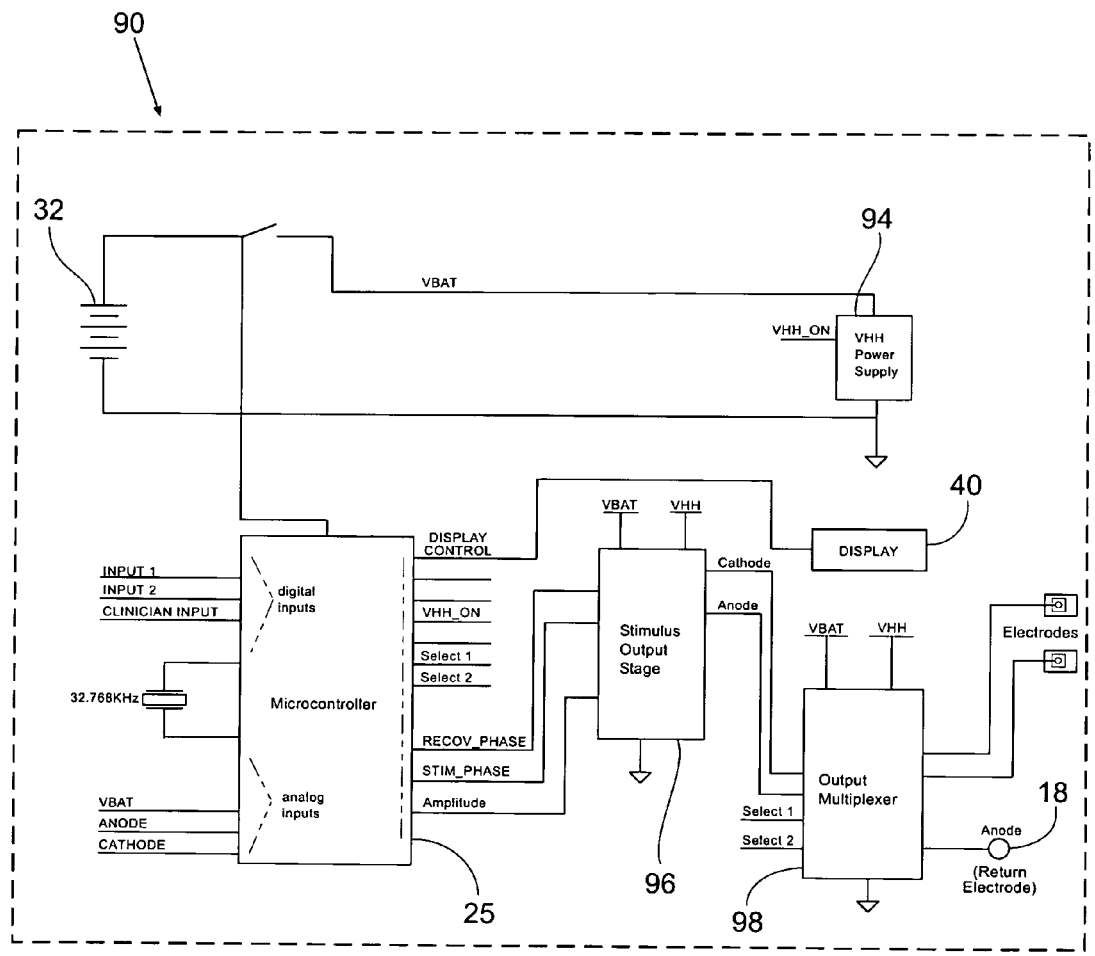
FIG. 7 is a block diagram of an embodiment of a circuit that the neurostimulation assembly shown in FIG. 1 may utilize.

FIG. 7 shows an embodiment of a block diagram circuit 90 for the neurostimulation assembly 10 that takes into account the desirable technical features of the neurostimulation assembly design discussed above. The circuit 90 can be grouped into functional blocks, which generally correspond to the association and interconnection of the electronic components.

In FIG. 7, five functional blocks are shown: (A) the Microprocessor Circuitry 24; (B) the Power Source 32; (C) the VHH Power Supply 94; (D) the Stimulus Output Stage(s) 96; and (E) the Output Multiplexer 98.

For each of these blocks, the associated functions, and possible key components and circuit description are now described.

A. The Microcontroller Circuitry

The microcontroller circuitry 24 may be responsible for the following functions:

(1) The timing and sequencing of most of the electronics pod 20 functions including the generation of stimulus pulses and the quantification of usage by the power source, (2) A/D converter to measure output pulse, power source voltage, and VHH voltage, (3) D/A converter may set the pulse amplitude, (4) Control for display 40 and/or illumination source 42, (5) And alternatively, control for a real time clock; the real time clock to provide a time signal to the microprocessor circuitry from the first powering of the electronics pod 20, and keep time without the presence of the power source 32, 72 for a predetermined amount of time, such as about one hour, day, week, or month, or more or less, as non-limiting examples.

The use of microcontroller based circuitry incorporating flash programmable memory allows the operating software of the neurostimulator as well as the stimulus parameters and settings to be stored in non-volatile memory (data remains safely stored even when the power source 32, 72, becomes fully discharged or is removed). The non-volatile memory is also used to store usage history information, and may also be located in the return electrode 70.

Although the microcontroller circuit 24 may be a single component, the firmware may be developed as a number of separate modules that deal with specific needs and hardware peripherals. The functions and routines of these software modules may be executed sequentially; but the execution of these modules may be timed and coordinated so as to effectively function simultaneously. The microcontroller operations that are associated directly with a given hardware functional block are described with that block.

The Components of the Microcontroller Circuit may include:

(1) A single chip microcontroller 25. This component may be a member of the Texas Instruments MSP430 family of flash programmable, micro-power, highly integrated mixed signal microcontroller. Likely family members to be used include the MSP430F1610, MSP430F1611, MSP430F1612, MSP430F168, MSP430F169, and the MSP430FG437. Each of these parts has numerous internal peripherals, and a micropower internal organization that allows unused peripherals to be configured by minimal power dissipation, and an instruction set that supports bursts of operation separated by intervals of sleep where the microcontroller suspends most functions.

(2) A miniature, quartz crystal for establishing precise timing of the microcontroller. This may be a 32.768 KHz quartz crystal, for example.

(3) Miscellaneous power decoupling and analog signal filtering capacitors.

B. Internal & External Power Source

The Power Source 32 and/or 72 (including associated microcontroller circuitry 24 actions) may be responsible for the following functions:

(1) monitor the battery voltage, (2) suspend stimulation when the power source voltage becomes very low, (3) discontinue stimulation when the power source has been used for a predetermined amount of time, e.g., one hour, day, week, month, two months, year, or whatever time is prescribed by the clinician, within a margin, (4) prevent (with single fault tolerance) the delivery of excessive current from the power source, and (5) provide power to the rest of the circuitry of the neurostimulation assembly, e.g., VHH power supply.

In one embodiment, power management controls are generally included with the electronics pod 20. As previously described, the circuitry 24 and/or return electrode 70 contains non-volatile memory, which is adapted to store power source usage information written by and read by the electronic pod 20.

(1) The electronics pod 20 and associated microcontroller circuitry 24 may periodically sample the power source 32, and periodically update usage data, such as the length of time, or the total number of pulses for which that the power source has been used. The circuitry 24 may also be adapted to read and write power source usage data to the non-volatile memory, 73.

C. VHH Power Supply

The VHH power supply 94 is generally responsible for the following functions:

(1) Provide the stimulus output stage 96 and multiplexer 98, if used, with a programmable DC voltage high enough to drive the required cathodic phase current through the electrode circuit plus the voltage drops across the stimulator stage, and possibly an output coupling capacitor. VHH is typically about 12 VDC to about 35 VDC.

The Components of the VHH Power Supply might include:

(1) Micropower, inductor based (fly-back topology) switch mode power supply; e.g., Texas Instruments TPS61045, Texas Instruments TPS61041, Linear Technology LT1615, or Linear Technology LT3459, for example.

(2) The microcontroller circuit 24 monitors VHH for detection of a VHH power supply failure, system failures, and optimizing VHH for the exhibited electrode circuit impedance.

The actual voltage of the internal stimulus power supply (VHH) may be dynamically adjusted by the stimulator to provide a minimum, but adequate operating overhead voltage for the stimulus output stage 96, thus minimizing the battery power consumption. Although the impedance presented by the lead 12, electrode 14, and the electrode to tissue interface varies little over time, the tissue to electrode impedance of the surface mounted return electrode 18 may vary and represents the majority of the electrode circuit impedance. A conventional, single inductor, flyback boost converter circuit topology may be used for the identified supply and loading conditions. This component may be the Sipex SP6691, or comparable switch mode power supply.

D. Stimulus Output Stage

Figure 8:
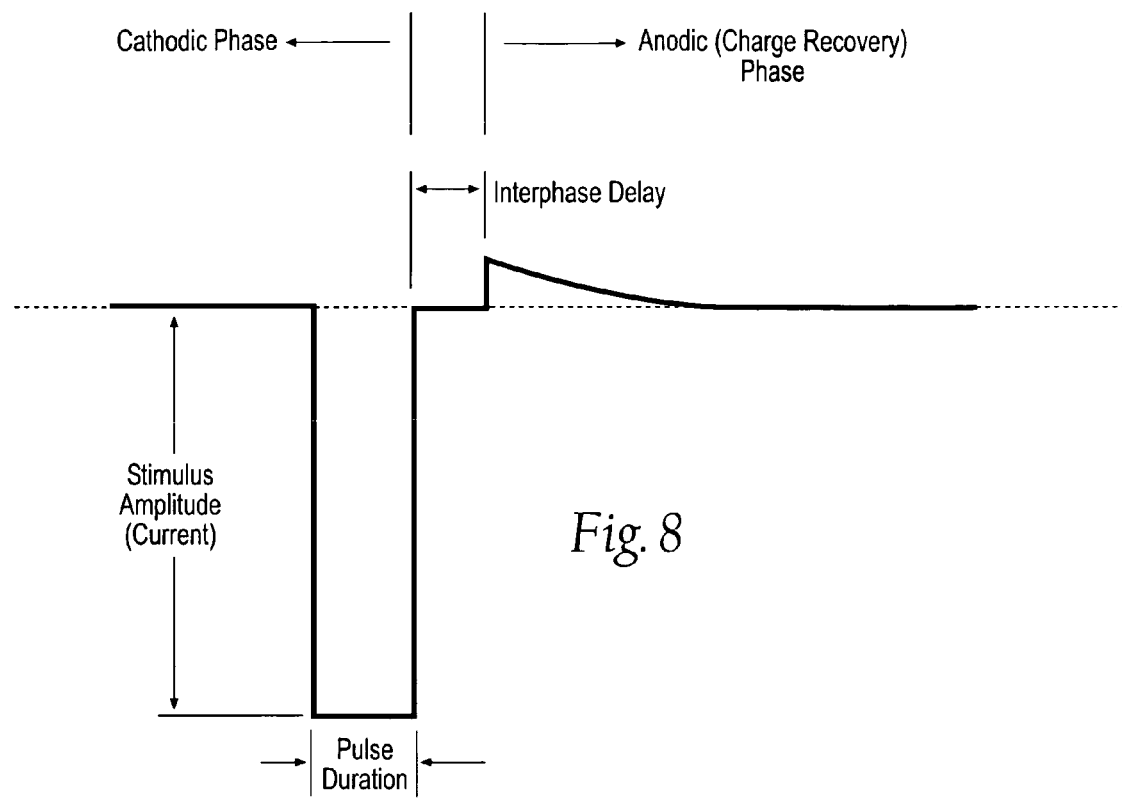
FIG. 8 is a graphical view of a possible biphasic stimulus pulse output of the neurostimulation assembly for use with the system shown in FIG. 1.

The Stimulus Output Stage(s) 96 is generally responsible for the following functions:

(1) Generate the identified biphasic stimulus current with selected cathodic phase amplitude, pulse width, and frequency. The recovery phase may incorporate a maximum current limit; and there may be a delay time (most likely a fixed delay) between the cathodic phase and the recovery phase (see FIG. 8). Typical currents (cathodic phase) vary from about 0.5 mA to about 20 mA based on the electrode construction and the nature of the tissue being stimulated. Electrode circuit impedances can vary with the electrode and the application, but are likely to be less than 2,000 ohms and greater than 100 ohms across a range of electrode types.

Two alternative configurations of the stimulus output stage will be described. In the first configuration:

(1) The cathodic phase current through the electrode circuit may be established by a high gain (HFE) NPN transistor with emitter degeneration shunted by switched shunting resistors to form a controlled current sink.

(2) The microcontroller circuit 24 monitors the cathode voltage to confirm the correct operation of the output coupling capacitor, to detect system failures, and to optimize VHH for the exhibited electrode circuit impedance; i.e., to measure the electrode circuit impedance.

In a second alternative configuration:

(1) A low-threshold N-channel MOSFET driven by an op-amp with fast enable/disable functions to provide a low quiescent current sink.

(2) A precision voltage reference of about 2.048V for both the microcontroller circuit external reference and the current sink reference.

(3) Switched shunting resistors may form the controlled current sink.

(4) The microcontroller circuit 24 monitors the cathode voltage to confirm the correct operation of the output coupling capacitor, to detect system failures, and to optimize VHH for the exhibited electrode circuit impedance; i.e., to measure the electrode circuit impedance.

In either configuration, the switched resistors could be replaced by a DAC, if available as an on-chip peripheral at the microcontroller. In either configuration, the start and ending of the cathodic phase current is timed by the microcontroller.

E. The Output Multiplexer

The output multiplexer 98 is required only if more than one electrode circuit is required. The output multiplexer is responsible for routing the anode and cathode connections of the Stimulus Output Stage 96 to the appropriate electrode, i.e., electrode(s) 14, and possibly return electrode 18, or both.

A representative output multiplexer configuration includes:

(1) A low ON resistance, micropower, dual 4×1 analog multiplexer; e.g. Maxim MAX4052, MAX384, Vishay DG412HS, or Pericom PS4066 or PS323 (with separate decoding logic or additional microcontroller address lines), for example, and (2) Microcontroller circuitry 24 selects the electrode connections to carry the stimulus current (and time the interphase delay) via address lines.

IV. The Electrodes and their Implantation

Figure 9:
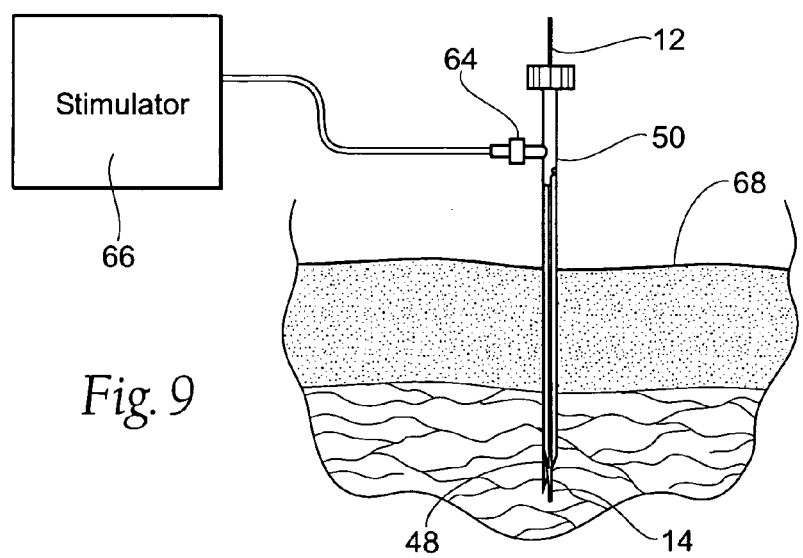
FIGS. 9 to 11 show the use of an electrode introducer to percutaneously implant an electrode in a targeted tissue region and for connection to a lead extension as shown in FIG. 3.

The configuration of the electrodes 14 and the manner in which they are implanted can vary. A representative embodiment will be described, with reference to FIGS. 9 to 11.

In the illustrated embodiment, each lead 12 may comprise a thin, flexible component made of a metal and/or polymer material. By "thin," it is contemplated that the lead 12 may not be greater than about 0.75 mm (0.030 inch) in diameter, although the diameter may be larger or smaller.

The lead 12 can comprise, e.g., one or more coiled metal wires with in an open or flexible elastomer core.

The wire can be insulated, e.g., with a biocompatible polymer film, such as polyfluorocarbon, polyimide, or parylene. The lead 12 are desirably coated with a textured, bacteriostatic material, which helps to stabilize the electrode in a way that still permits easy removal at a later date and increases tolerance.

The electrode 14 are electrically insulated everywhere except at one (monopolar), or two (bipolar), or three (tripolar), for example, conduction locations near its distal tip. Each of the conduction locations may be connected to one or more conductors that run the length of the lead 12, proving electrical continuity from the conduction location through the lead 12 to the electronics pod 20. The conduction location may comprise a de-insulated area of an otherwise insulated conductor that runs the length of an entirely insulated electrode. The de-insulated conduction region of the conductor can be formed differently, e.g., it can be wound with a different pitch, or wound with a larger or smaller diameter, or molded to a different dimension. The conduction location of the electrode may comprise a separate material (e.g., metal or a conductive polymer) exposed to the body tissue to which the conductor of the wire is bonded.

In an alternative configuration, the lead 12 does not utilize an extension 12, rather the lead 12 is electrically connected to the electronics pod 20 or carrier 16 through an automated connection method that connects and terminates the electrode 14.

The electrode(s) 14 and lead 12 are desirably provided in sterile packages and desirably possess mechanical properties in terms of flexibility and fatigue life that provide an operating life free of mechanical and/or electrical failure, taking into account the dynamics of the surrounding tissue (i.e., stretching, bending, pushing, pulling, crushing, etc.). The material of the electrode desirably discourages the in-growth of connective tissue along its length, so as not to inhibit its withdrawal at the end of its use. However, it may be desirable to encourage the in-growth of connective tissue at the distal tip of the electrode, to enhance its anchoring in tissue.

Figure 10:
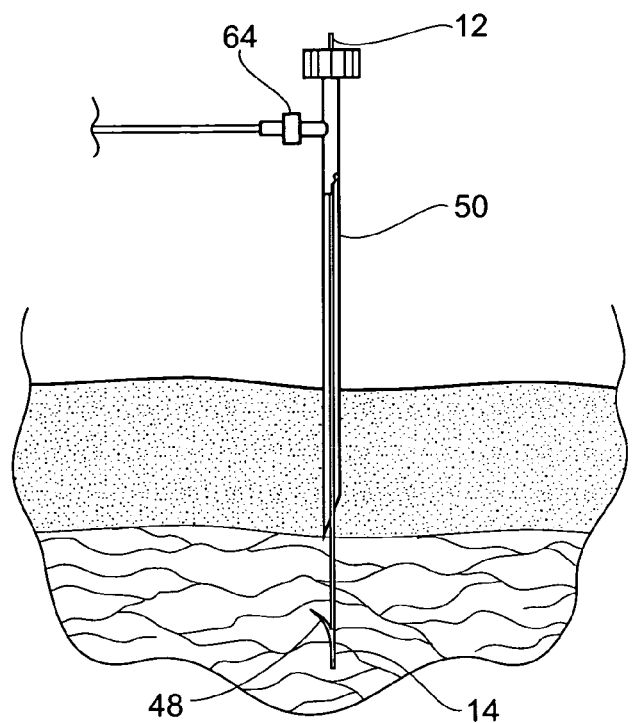
Figure 11:
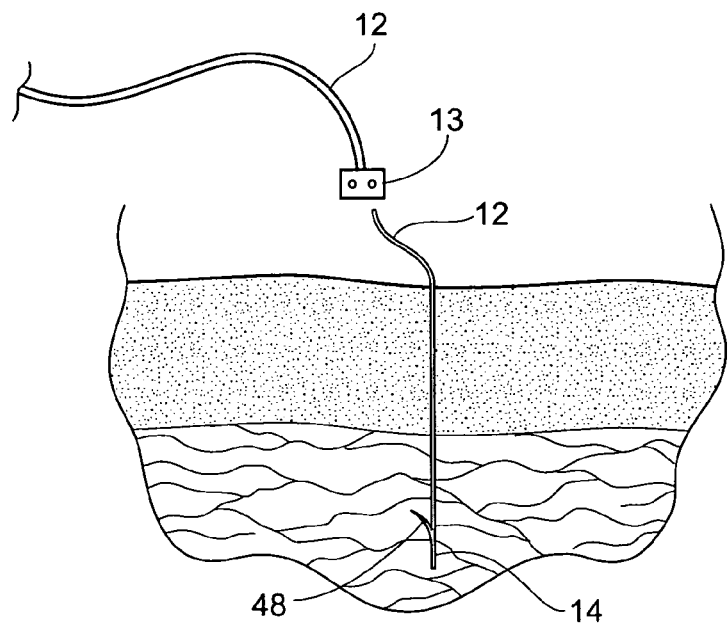

Furthermore, the desired electrode 14 may also include, at its distal tip, an anchoring element 48 (see FIGS. 10 and 11). In the illustrated embodiment, the anchoring element 48 takes the form of a simple barb or bend. The anchoring element 48 is sized and configured so that, when in contact with tissue, it takes purchase in tissue, to resist dislodgement or migration of the electrode out of the correct location in the surrounding tissue. Desirably, the anchoring element 48 is prevented from fully engaging body tissue until after the electrode 14 has been deployed. The electrode is not deployed until after it has been correctly located during the implantation (installation) process, as will be described in greater detail later.

In one embodiment, the lead 12 can include a metal stylet within its core. Movement of the stylet with respect to the body of the electrode and/or an associated introducer (if used) is used to deploy the electrode by exposing the anchoring element 48 to body tissue. In this arrangement, the stylet is removed once the electrode 14 is located in the desired region.

In the illustrated embodiment (see FIGS. 10 and 11), an electrode 14 may be percutaneously implanted housed within electrode introducer 50 (i.e., a hypodermic needle). The electrode introducer 50 comprises a shaft having sharpened needle-like distal tip, which penetrates skin and tissue leading to the targeted tissue region. The lead 12 may be loaded (it may be preloaded and provided in a kit) within a lumen in the introducer 50, with the anchoring element 48 shielded from full tissue contact within the shaft of the introducer 50 (see FIG. 9). In this way, the introducer can be freely manipulated in tissue in search of a desired final electrode implantation site (see FIG. 10) before deploying the electrode and withdrawing the introducer 50 (see FIG. 11).

The electrode introducer 50 may be insulated along the length of the shaft, except for those areas that correspond with the exposed conduction surfaces of the electrode 14 housed inside the introducer 50. These surfaces on the outside of the introducer 50 are electrically isolated from each other and from the shaft of the introducer 50. These surfaces may be electrically connected to a connector 64 at the end of the introducer body (see FIGS. 9 and 10). This allows connection to a stimulating circuit 66 (see FIG. 9) during the implantation process. The stimulating circuit 66 may comprise a stand along stimulator, or the neurostimulation assembly 10 may be the stimulating circuit. Applying stimulating current through the outside surfaces of the introducer 50 provides a close approximation to the response that the electrode 14 will provide when it is deployed at the current location of the introducer 50.

The electrode introducer 50 is sized and configured to be bent by hand prior to its insertion through the skin. This will allow the physician to place an electrode 14 in a location that is not in an unobstructed straight line with the insertion site. The construction and materials of the electrode introducer 50 allow bending without interfering with the deployment of the lead 12 and withdrawal of the electrode introducer 50, leaving the electrode 14 in the tissue.

V. Installation of the Neurostimulation Assembly

Prior to installation, a clinician identifies a particular muscle(s) and/or neural region(s) to which a prescribed therapy using the neurostimulation assembly 10 will be applied. Once the particular muscle(s) and/or nerve(s) and/or tissue region or regions are identified, the clinician proceeds to percutaneously implant one or more electrodes 14 and leads 12, one by one, through the desired skin region 68. While each electrode 14 is implanted, the electrode introducer 50 applies a stimulation signal until a desired response is achieved indicating the desired placement, at which time the electrode 14 is deployed and the introducer 50 is withdrawn.

Figure 4:
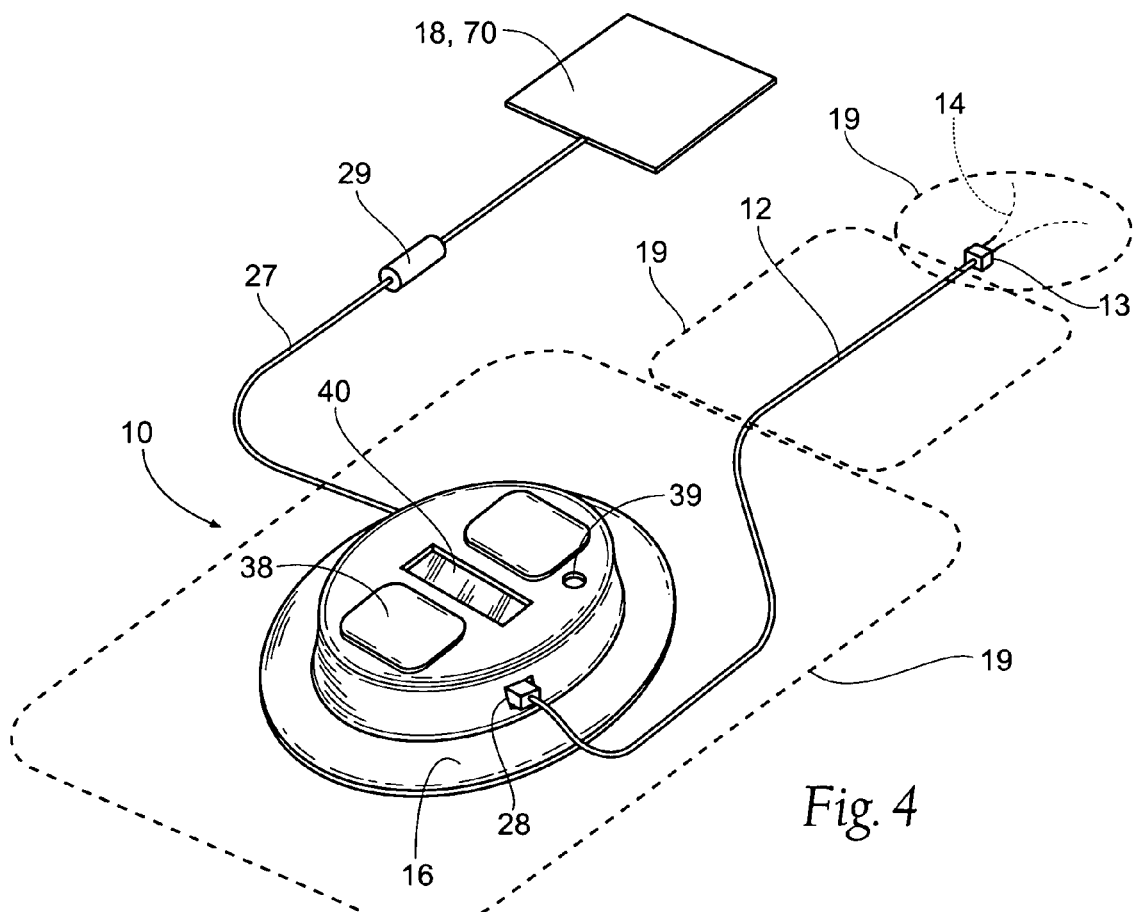
FIG. 4 is a perspective view of an embodiment of a neurostimulation assembly of the type shown in FIG. 1, showing configurations of covering bandages to secure the electrodes, lead, and assembly in place for use.

Upon implanting each electrode (see FIG. 4, for example), the clinician is able to route the extension lead 12, if used, to a lead connector 28 on the electronics pod 20 (or carrier 16).

The following illustration will describe the use of a neurostimulator assembly 10 that will be carried or worn on the patient's exterior skin surface. It is to be appreciated that the neurostimulator assembly 10 could be carried by the patient or temporarily secured to a bed or other structure and the lead extensions 12 extend to the assembly 10. The assembly 10 is placed around an arm or leg (e.g., with the use of a strap), or on the skin in a desirable region, that allows electrical connectivity to the electrode(s) 14, lead 12, and associated connector 28 (see FIGS. 2A through 3). The carrier 16 may be secured in place with pressure sensitive adhesive 18 on the bottom of the carrier 16, or held in place with a covering tape, or with a strap, as previously described. As previously stated, the adhesive region desirably contains a bacteriostatic sealant that prevents skin irritation or superficial infection, which could lead to premature removal.

After implanting one or more electrodes 14 and placing a return electrode 18, 70, on the skin surface, the clinician would be able to route the lead 12 to the electronics pod 20, and couple the return electrode to the connector 29 to complete the stimulation path. The neurostimulation assembly 10 is ready for use.

VI. System Kits

Figure 12:
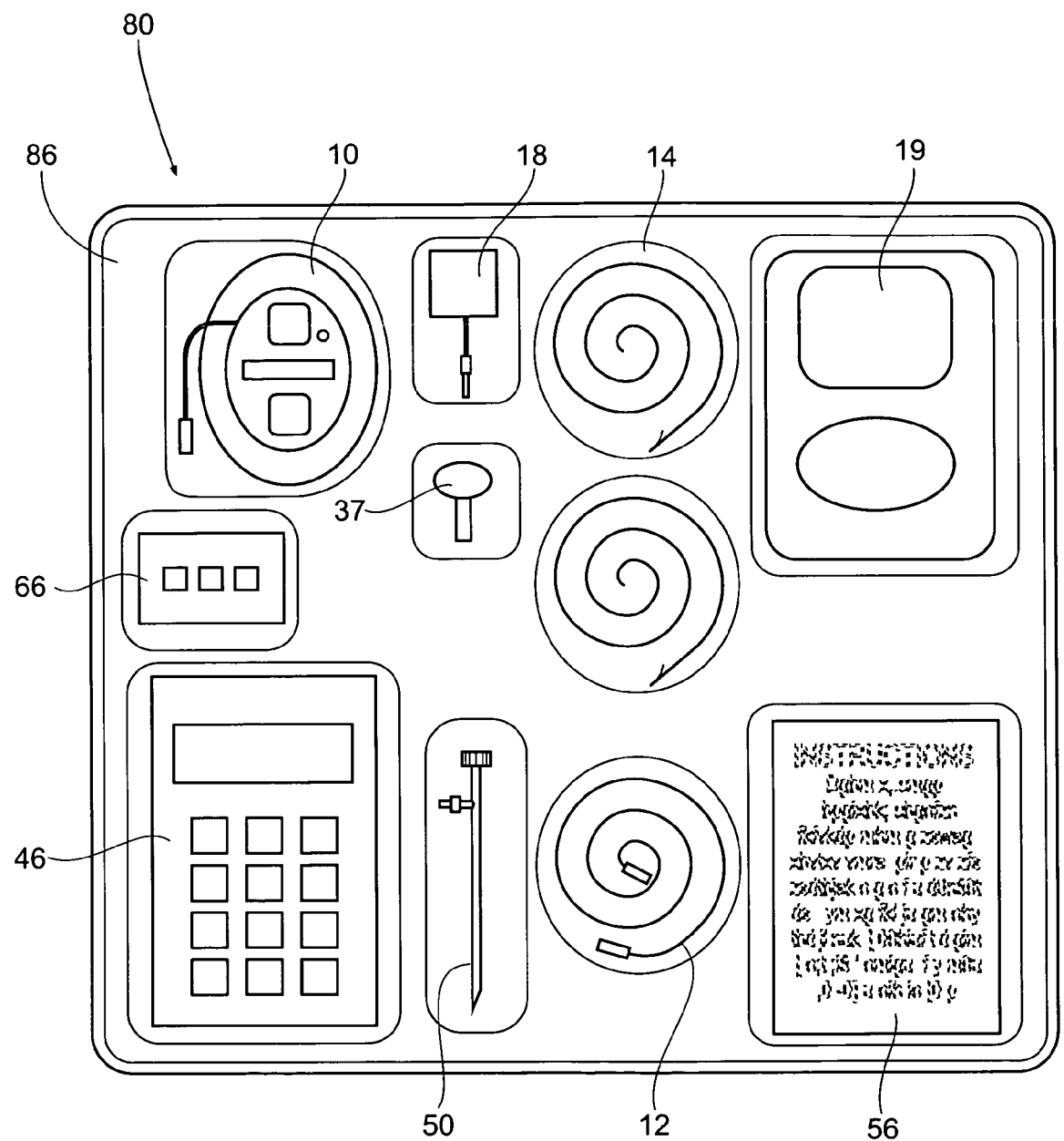
FIG. 12 is a plan view of an embodiment of a kit packaging the neurostimulation assembly and associated components for use, along with instructions for use.
Figure 13:
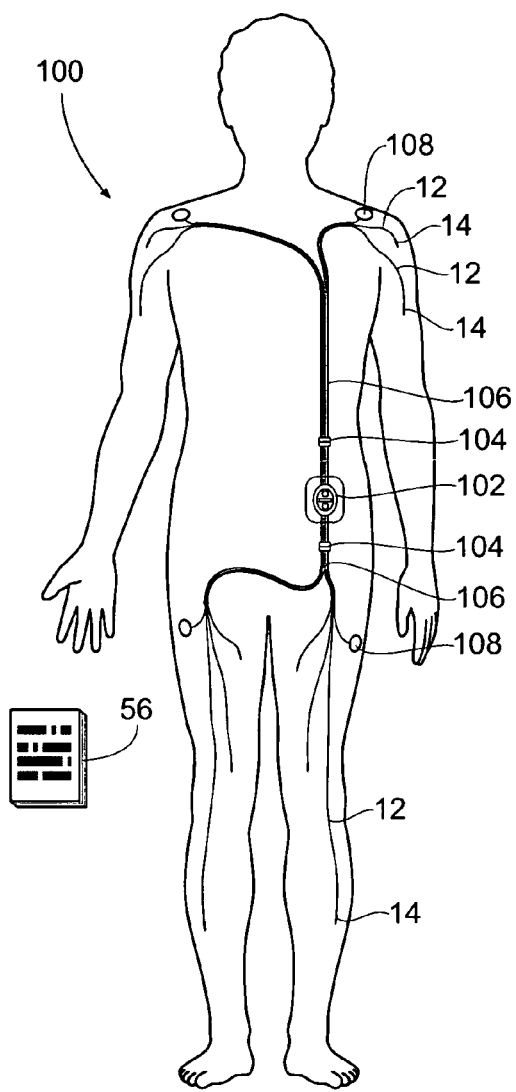
FIG. 13 is an anatomical view showing an alternative configuration of a neurostimulation assembly and system, the system including a harnessed multi-channel stimulation assembly capable of providing coordinated neurostimulation to multiple regions of the body.
Figure 14:
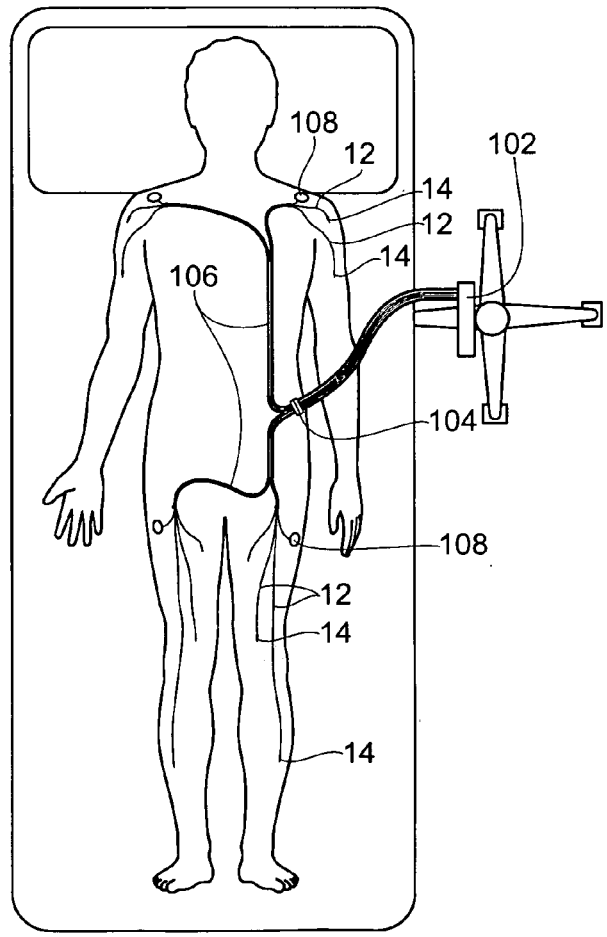
FIG. 14 is an anatomical view of the system shown in FIG. 13, showing the harnessed multi-channel neurostimulation assembly configured to be held on a movable stand next to the patient.
Figure 15:
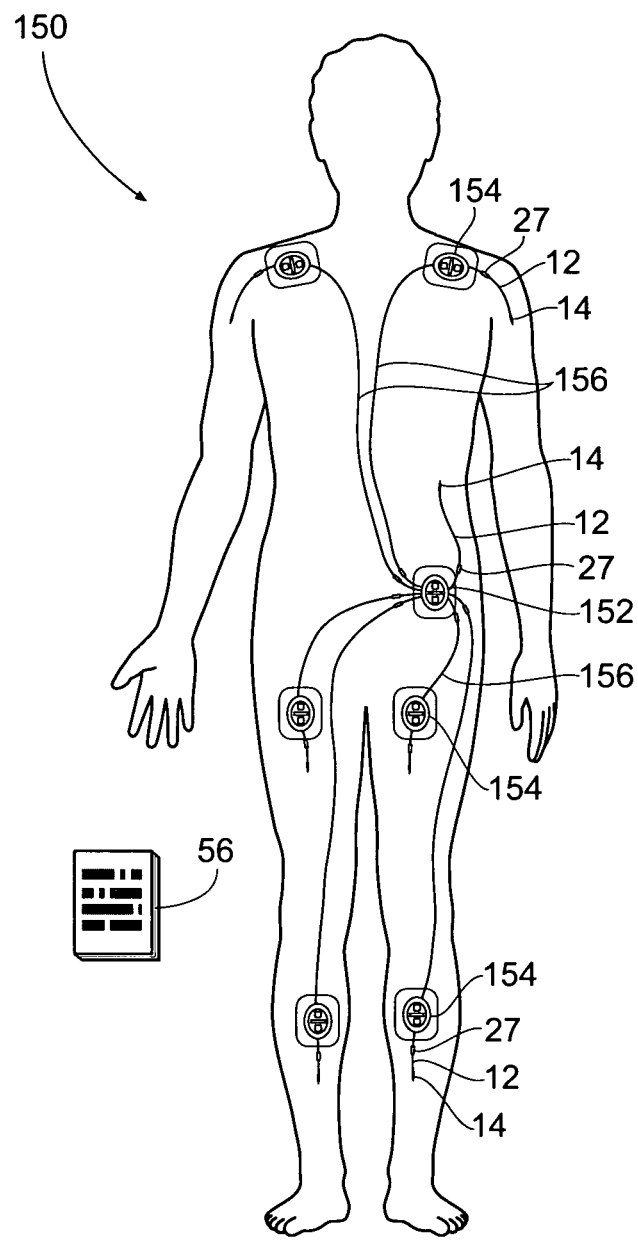
FIG. 15 is an anatomical view showing an additional alternative configuration of a neurostimulation assembly and system, the system including a master neurostimulation stimulation assembly and one or more slave neurostimulation assemblies, with the master assembly capable of providing coordinated control of multiple slave neurostimulation assemblies, the system capable of providing coordinated neurostimulation to multiple regions of the body.

As FIG. 12 shows, the various devices and components just described can be consolidated for use in one or more functional kit(s) 82. The kit can take various forms. In the illustrated embodiment, the kit 82 comprises a sterile, wrapped assembly. The kit 82 includes an interior tray 86 made, e.g., from die cut cardboard, plastic sheet, or thermo-formed plastic material, which hold the contents. Kit 82 also desirably includes instructions for use 56 for using the contents of the kit to carry out a desired therapeutic and/or diagnostic and/or functional objectives.

The instructions 56 can, of course vary. The instructions 56 shall be physically present in the kits, but can also be supplied separately. The instructions 56 can be embodied in separate instruction manuals, or in video or audio tapes, CD's, and DVD's. The instructions 56 for use can also be available through an internet web page.

The arrangement and contents of the kit 82 can vary. For example, FIG. 12 shows a kit 82 containing the neurostimulation assembly 10. The instructions for use 56 in the kit 82 may direct a clinician to place the neurostimulation assembly 10, implant the electrode 14, couple the electrode 14 to the lead 12, couple the lead 12 to the assembly 10, and place the return electrode 18 and couple the return electrode to the assembly 10. The instructions may also include instructions for the user in the operation of the neurostimulation assembly 10. Kit 82 may also include an extension lead 12, and one or more electrodes 14.

As FIG. 5 shows, external desktop or handheld (desirably also battery powered) preprogrammed and/or programmable instruments 46 can be used to program stimulus regimes and parameters into the neurostimulation assembly 10, or to download recorded data from the neurostimulation assembly 10 for display and further processing. Instructions for use 56 may describe options for the instruments 46 to communicate with the neurostimulation assembly 10, e.g., by a cable connection 58, wireless coupling 59, e.g., by radio frequency magnetic field coupling, by infrared, or by RF wireless, for example. The communications cable 58 may be adapted to provide power to the neurostimulation assembly 10 during programming, as well as communications with the circuitry 24 of the neurostimulation assembly 10. The external programming instrument 46 can also be a general purpose personal computer or personal digital device fitted with a suitable custom program and a suitable cable or interface box for connection to the communications cable 58.

The programming instruments 46 allow a clinician one option for customizing the stimulus parameters and regime timing residing in an individual neurostimulation assembly 10 according the specific needs of the user and the treatment goals of the clinician. The neurostimulation assembly 10 can, once customized, be disconnected from the programming system, allowing portable, or skin worn operation, as already described. The programming instruments also allow the retrieval of usage information allowing the clinician to accurately assess patient compliance with the prescribed treatment course or regime. Alternatively, and as previously described, the clinician may use the push buttons 38, display 40, and/or access through the use of the programming mode key 37 to program the stimulus parameters and timing and to retrieve key usage data.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A neurostimulation assembly comprising:
   at least one electrode sized and configured for implantation in a targeted neural or muscular tissue region,
   a lead electrically coupled to the electrode and including a connection element adapted to electrically couple to a carrier, the carrier sized and configured to be carried by the patient,
   an electronics pod removably carried on-board the carrier, the electronics pod including circuitry configured to generate a stimulation pulse,
   a power source electrically coupled to the circuitry,
   a return electrode adapted to be electrically coupled to the carrier,
   instructions prescribing the release and replacement of the return electrode according to a preset schedule, and
   an electrode connection element carried on-board the carrier that is electrically coupled to the electronics pod, the electrode connection element being sized and configured to electrically engage at least a portion of the exposed region of the lead to electrically couple the electrode to the electronics pod to percutaneously apply the stimulation pulse to the tissue region.

2. An assembly according to claim 1:
wherein the carrier is sized and configured to hold the power source.

3. An assembly according to claim 2:
wherein the power source is at least on of a non-removable and non-replaceable and non-rechargeable power source.

4. An assembly according to claim 1:
wherein the return electrode is sized and configured to hold the power source.

5. An assembly according to claim 4:
wherein the power source is at least on of a non-removable and non-replaceable and non-rechargeable power source.

6. An assembly according to claim 4:
wherein the preset schedule comprises the replacement of the return electrode repeated at least on about a daily or weekly or monthly basis.

7. An assembly according to claim 1:
wherein the electronics pod carried on-board the carrier is sized and configured for selective release from the carrier.

* * * * *